United States Patent [19]

Mantegani et al.

[11] Patent Number: 4,859,678
[45] Date of Patent: Aug. 22, 1989

[54] N-OXIDE ERGOLINES AS ANTIHYPERTENSIVE AGENTS

[75] Inventors: Sergio Mantegani, Milan; Enzo Brambilla, Mariano Comense; Aldemio Temperilli; Daniela Ruggieri, both of Milan; Patricia Salvati, Arese, all of Italy

[73] Assignee: Farmitalia Carlo Erba, Milan, Italy

[21] Appl. No.: 210,420

[22] Filed: Jun. 21, 1988

[30] Foreign Application Priority Data

Jun. 24, 1987 [GB] United Kingdom ................ 8714767

[51] Int. Cl.$^4$ .................. A61K 31/505; A61K 31/48; C07D 403/14; C07D 457/08
[52] U.S. Cl. .................................... 514/269; 544/310; 514/288; 546/67; 546/68
[58] Field of Search .................... 546/67, 68; 544/310; 524/288, 269

[56] References Cited

U.S. PATENT DOCUMENTS

| 4,657,914 | 4/1987 | Bernardi et al. | 546/67 |
| 4,690,929 | 9/1987 | Bernardi et al. | 546/67 |
| 4,801,588 | 1/1989 | Temperilli et al. | 548/421 |

FOREIGN PATENT DOCUMENTS

| 897661 | 9/1983 | Belgium | 546/67 |
| 126968 | 12/1984 | European Pat. Off. | 546/68 |
| 3700825 | 7/1987 | Fed. Rep. of Germany | |
| 2120242 | 11/1983 | United Kingdom | 546/67 |
| 2185743 | 7/1987 | United Kingdom | |

OTHER PUBLICATIONS

Stuetz et al., CA80-121173u (1974) "Novel Approach to Cyclic β-Carbonyl Enamines".
Ponikvar et al., CA98-34825m (1983) "N-6-Oxides of 9,10-Dihydroergot Alkaloids".
Bernardi et al., CA 101-7507h (1984) "7-Cyanoergolines".
Bernardi et al., CA102-149582y "Ergoline Derivatives".
Nordmann et al., CA106-156750n (1987) "Synthesis of (5R, 8S, 10R)-6-(allyloxy)-and . . . ".
Ziegler et al., CA107-217905m (1987) "Preparation of 8α-(Acylamino) Ergolines as Neuroleptics . . . ".
Ziegler et al., CA 107-198727 m (1987) "Preparation and Formulation of 8α-Acylamino . . . " Nordmann et al., Helv. Chim. Acta., vol. 69 (1986) 246–250.
Stütz et al., Tetrahedron Letters, No. 51, pp. 5095–5098, 1973.
Noller, Chemistry of Organic Compounds, 1965, pp. 672–673.

*Primary Examiner*—Cecilia Shen
*Attorney, Agent, or Firm*—Oblon, Spivak, McClelland, Maier & Neustadt

[57] ABSTRACT

An ergoline derivative of the formula I:

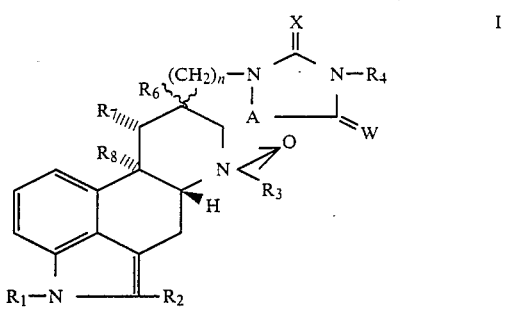

wherein $R_1$ represents hydrogen or a methyl group; $R_2$ represents hydrogen or a halogen atom, a methyl, cyano or phenyl group or an alkylthio group having from 1 to about 4 carbon atoms; $R_3$ represents a hydrocarbon group having from 1 to about 4 carbon atoms; $R_4$ represents hydrogen, a phenyl group or a hydrocarbon group having from 1 to about 4 carbon atoms; wherein either (a) $R_6$ and $R_7$ represent a valence bond or hydrogen atoms and $R_8$ represents a hydrogen atom or a methoxy group, or (b) $R_6$ represents a hydrogen atom and $R_7$ and $R_8$ taken together represent a valence bond; W represents an oxygen atom or an imino group; A represents a group of the formula $CHR_5$, $CH=CR_5$ or $CH_2CHR_5$ wherein $R_5$ represents a hydrogen atom or an alkyl group having from 1 to about 4 carbon atoms; X represents an oxygen or sulphur atom or an imino group; and n is 0, 1 or 2; or a pharmaceutically acceptable salt thereof.

7 Claims, No Drawings

N-OXIDE ERGOLINES AS ANTIHYPERTENSIVE AGENTS

BACKGROUND OF THE INVENTION

1. Field of the Invention:

This invention relates to N-oxide ergolines, a process of preparing the same and to pharmaceutical compositions containing the same.

2. Description of the Background:

At present, certain ergoline derivatives are used as anti-hypertensive compounds. For example, EP 0126968 discloses compounds such as 1-[6-methyl -Δ-9,10-ergolen -8β- yl)methyl]-2,4-(1H,3H)-pyrimidine dione. However, such compounds exhibit a rapid onset of antihypertensive effect with short duration of action.

Thus, a need continues to exist for ergoline derivatives which exhibit a longer duration of antihypertensive effect with a slower onset of effect.

SUMMARY OF THE INVENTION

Accordingly, it is an object of the present invention to provide ergoline derivatives having a marked prolongation of pharmacological effect.

It is, in particular, an object of this invention to provide ergoline derivatives exhibiting slower onset and larger duration of antihypertensive effect.

Further, it is also an object of this invention to provide a process for preparing the ergoline derivatives.

Moreover, it is also an object of this invention to provide pharmaceutical compositions containing the ergoline derivatives.

DETAILED DESCRIPTION OF THE PREFERRED EMBODIMENTS

The present invention provides ergoline derivatives of the formula I:

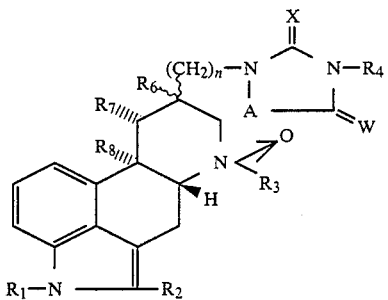

wherein $R_1$ represents a hydrogen atom or a methyl group; $R_2$ represents a hydrogen or halogen atom, a methyl, cyano or phenyl group or an alkylthio group having from 1 to about 4 carbon atoms; $R_3$ represents a hydrocarbon group having from 1 to about 4 carbon atoms; either (a) each of $R_6$ and $R_7$ represents a hydrogen atom or, taken together, $R_6$ and $R_7$ represent a valence bond and $R_8$ represents a hydrogen atom or a methoxy group, or (b) $R_6$ represents a hydrogen atom and $R_7$ and $R_8$ taken together represent a valence bond; W represents an oxygen atom or an imino group; A represents a group of the formula $CHR_5$, $CH=CR_5$ or $CH_2CHR_5$ wherein $R_5$ represents a hydrogen atom or an alkyl group having from 1 to about 4 carbon atoms; X represents an oxygen or sulphur atom or an imino group; n is 0, 1 or 2; and $R_4$ represents hydrogen atom, a hydrocarbon group having from 1 to about 4 carbon atoms or a phenyl group.

Pharmaceutically acceptable salts of these ergoline derivatives are also provided by the present invention.

In the definition of $R_2$, the term "halogen" should preferably be construed to encompass chlorine and bromine atoms; nevertheless, the term "halogen" also encompasses a fluorine atom.

In the definition of $R_3$ and $R_4$, the hydrocarbon group having from 1 to 4 carbon atoms includes alkyl, cycloalkyl, cyclopropylmethyl and unsaturated (both ethylenically and acetylenically) groups. Representative moieties include methyl, ethyl, n-propyl, isopropyl, butyl, t-butyl, cyclopropyl, vinyl, allyl and propargyl.

The term "pharmaceutically acceptable salts" refers to those salts which retain the biological effectiveness and properties of the free bases and which are not biologically or otherwise undesirable. Such salts may be formed with inorganic acids such as hydrochloric, hydrobromic, sulphuric, nitric, or phosphoric acids; or with organic acids such as acetic, pripionic, glycolic, pyruvic, oxalic, malic, malonic, succinic, fumaric, tartaric, citric, benzoic, cinnamic, mandelic, methanesulphonic or salicyclic acids.

The substituents $R_1$, $R_2$, $R_4$, $R_5$ and $R_6$ preferably represent hydrogen atoms. Preferably $R_3$ is a methyl group, n is 1 and $R_7$ and $R_8$ taken together represent a bond. Preferably W and X represent oxygen atoms and A represents a group of the formula $-CH_2-$ or $-CH_2-CH_2-$.

The invention further provides a process for the preparation of a compound of the general formula I as defined above, the process comprising the N-oxidation of an ergoline derivative of the formula II:

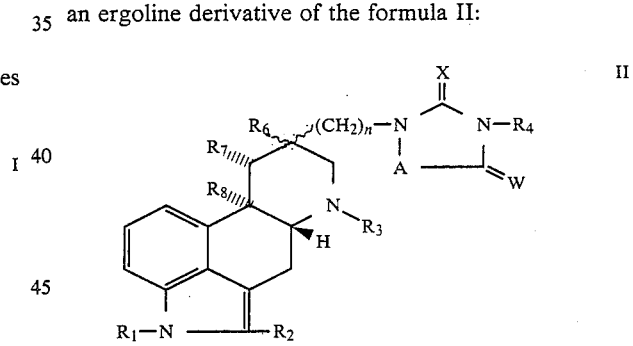

wherein $R_1$, $R_2$, $R_3$, $R_4$, $R_6$, $R_7$, $R_8$, A, W, X and n are as defined above.

The oxidation may be carried out with organic peracids such as perbenzoic, monoperphthalic, m-chloroperbenzoic, peracetic, performic or trifluoroperacetic acids, optionally formed in situ, in a solvent such as chloroform, tetrahydrofuran or dimethylformamide, for a period of from 1 to 24 hours at a temperature of from 0° to 40° C. The oxidation may alternatively be carried out by treating a compound of formula II with a solution of hydrogen peroxide in the presence of a catalyst such as tungstic acid, a homopolytungstic acid, a heteropolytungstic acid, molybdic acid, a homopolymolybdic acid or a heteropolymolybdic acid, or an alkali metal salt of one of these acids, at a pH of from 0.5 to 5.

The ergoline derivatives of the formula II are known compounds described in European Patent Specification No. 126,968, or may be prepared by established procedures starting from known compounds according to the methods described in the European Patent Specification.

Free base forms of the compounds of formula I may be converted into acid addition salts forms in a conventional manner and vice versa.

The compounds of the present invention and their pharmaceutically acceptable salts are useful as antihypertensive agents with a slow onset of action and long lasting activity.

The present invention will now be further illustrated by the following Examples which are provided for purposes of illustration only and are not intended to limit the present invention.

ANTIHYPERTENSIVE ACTIVITY: METHODS

Intrarterial measurements of mean blood pressure (MBP) were performed through catheters (PE 50, Clay Adams) implanted in the rat right carotid artery under halothane anesthesia. Twenty four hours after surgery, the animals were placed in Ballman cages and the arterial cannula was connected via a pressure transducer to a Beckman blood pressure recorder for continuous monitoring of mean blood pressure. MBP was recorded before the oral administration (basal values) and at 15-30-60-120-240 minutes until 12 hours after treatment. Groups of 7 to 8 rats were orally treated with a single dose of the test compound of vehicle, methocel 0.5% w/v (0.2 ml/100 g b.w.). The $ED_{25}$ was calculated for each compound from the dose-response regression line.

RESULTS

The $ED_{25}$ (dose lowering mean blood pressure of 25 mmHg) obtained with some compounds of formula I are reported in Table 1.

As reference standard drugs, two prior art ergoline derivatives described by EP 0126968 were also tested.

By comparison of each prior art compound with the corresponding N-oxide derivative of the present invention, it can be observed that the $ED_{25}$ values are similar (Table 1) but the N-oxide compounds showed a marked prolongation of antihypertensive effect, that is a much slower onset and a much longer duration of action, as is evident from the data reported in Table 2. In fact, the mean blood pressure decrease induced by the two derivatives of the present invention was still significant 10 to 12 hours after dosing, whereas with the prior art compounds the hypotensive effect lasted only 5 to 6 hours. The oral orientative acute toxicity ($LD_{50}$) in mice (evaluated in the Irwin test) of the compounds of the formula I was higher than 800 mg/kg.

TABLE 1

| COMPOUND | $ED_{25}$ (mg/Kg$^{-1}$ p.o.) |
|---|---|
| 1-[(6-methy -Δ- 9,10-ergolen-8β-yl)methyl]-2,4-(1H,3H)dihydro-pyrimidine diole; EP 0126989, Example 40 | 0.046 |
| 1-[(6-methyl-Δ- 9,10-ergolen-8β-yl)methyl]-2,4-(1H,3H)-dihydro-pyrimidine-dione-N—6-oxide; present invention, Example 1 | 0.050 |
| 1-[(6-methyl-Δ- 9,10-ergolen -8β-yl)methyl]-2,4-imidazolidinedione; EP 0126968, Example 41 | 0.190 |
| 1-[(6-methyl-Δ- 9,10-ergolen -8β-yl) methyl]-2,4-imidazolidinedione-N—6-oxide; present invention, Example 2 | 0.198 |

TABLE 2

| | Decrease in mean blood pressure (ΔmmHg) | | | | | | | | | | | |
|---|---|---|---|---|---|---|---|---|---|---|---|---|
| | | | | | Time | | | | | | | |
| Compound | 0* | 15' | 30' | 1 h | 2 h | 3 h | 4 h | 5 h | 6 h | 8 h | 10 h | 12 h |
| Standard, ex 40 of EP 0126968 0.125 mg/kg p.o. | 176.7 | −22.9 | −34.5 | −33.9 | −37.3 | −34.5 | −42.7 | −28.9 | −25.5 | −10.5** | −7.3** | −6.7** |
| Present invention example 1 0.5 mg/kg p.o. | 173.1 | −12.2** | −21.0 | −32.2 | −35.5 | −45.1 | −55.1 | −58.5 | −54.3 | −44.3 | −35.5 | −27.2 |
| Standard, ex 41 of EP 0126968 0.25 mg/Kg p.o. | 186.1 | −26.8 | −31.4 | −29.6 | −37.5 | −35.7 | −31.4 | −15.7 | −14.6** | −2.5** | −6.5** | −9.4** |
| Present invention example 2 1 mg/kg p.o. | 178.1 | −23.1 | −27.5 | −35.9 | −34.1 | −35.0 | −38.4 | −36.5 | −34.1 | −27.8 | −22.5 | −16.2 |

*Mean blood pressure before treatment
**Not significant value

The invention further provides a pharmaceutical composition containing a therapeutically effective amount of a compound of formula I or a pharmaceutically acceptable salt thereof in admixture with a pharmaceutically acceptable diluent or carrier. The administration of compounds I and their non-toxic pharmaceutically acceptable acid addition salts or mixtures thereof may be achieved either parenterally or orally, preferably orally.

As used herein, the term "effective amount" encompasses those amounts which yield the desired activity without causing adverse side effects. However, an effective dosage is in the range of about 0.001 to 0.5 mg/kg day, preferably 0.1 to 0.25 mg/kg day.

The pharmaceutical carriers which are typically employed with the compounds of the invention may be solid or liquid and are generally selected dependent on the planned manner of administration. Thus, for example, solid carriers include lactose, sucrose, gelatin and agar and the like, while liquid carriers include water, syrup, peanut oil and olive oil and the like.

The combination of the selected compound and the carrier may be fashioned into numerous acceptable forms such as tablets, capsules, suppositories, solutions, emulsion, powders and syrups.

The following additional examples are also provided only for purposes of illustration and are not intended to limit the present invention.

EXAMPLES

Example 1

1-[6-methyl-Δ-9,10-ergolen-8β-yl)methyl]-2,4-(1H,3H)dihydro-pyrimidinedione-N6-oxide A solution of 2.75 g. of 1-[(6-methyl-Δ-9.10-ergolen-8β-yl)methyl]-2,4-(1H,3H)dihydro-pyrimidinedione, in 100 ml of tetrahydrofuran and 30 ml of dimethylformamide was treated with 1.7 g of m-chloroperbenzoic acid in 20 ml of tetrahydrofuran. The solution was set aside at room temperature for two hours then the solvent was evaporated under high vacuum.

Addition of 0.9 g of sodium bicarbonate gave, after filtration and crystallization from methanol, 2 g of the title compound, m.p. 175–177° C.

Example 2

1-[(6-methyl-Δ-9,10-ergolen-8β-yl)methyl]-2,4-imidazolidinedione-N6-oxide

Repeating Example 1 but employing 1-[(6-methyl-Δ-9,10-ergolen-9β-yl)methyl]-2,4-imidazolinedione instead of 1-[(6-methyl-Δ-9,10-ergolen-8β-yl)methyl]-2,4-(1H,3H)-pyrimidinedione, the title compound was obtained in 73% yield, m.p. 159–162° C.

Example 3

1-[(6-methylergolin-8β-yl)]-2,4-(1H,3H)-dihydro pyrimidinedione-N6-oxide

Repeating Example 1 but using 1-[(6-methylergolin-8β-yl)]-2,4-(1H,3H)dihydro-pyrimidinedione instead of 1-[(6-methyl-Δ-9,10-ergolen-8β-yl)methyl]-2,4-(1H,3H)-pyrimidinedione, the title compound was obtained in 57% yield, m.p. 138–140° C.

Example 4

1-[(6-methylergolin-8β-yl)methyl]-2,4-(1H,3H)-dihydro pyrimidinedione-N6-oxide

Repeating Example 1 but using 1-[(6-methylergolin-8β-yl)methyl]-2,4-(1H,3H)dihydro pyrimidinedione instead of 1-[(6-methyl-Δ-9,10-ergolen-8β-yl)methyl]-2,4-(1H,3H)-pyrimidinedione the title compound was obtained in 75% yield, m.p. 139–141° C.

Example 5

1-[(6-methylergolin-8β-yl)methyl]-2,4-imidazolidinedione-N-oxide

Repeating Example 1 but using 1-[(6-methylergolin-8β-yl)methyl]-2,4-imidazolidinedione instead of 1-[(6-methyl-Δ-9,10-ergolen-8β-methyl]-2,4-(1H,3H)-pyrimidinedione the title compound was obtained in 63% yield, m.p. 163–165° C.

Example 6

1-[(6-methylergolin-8β-)ethyl]-2,4-(1H,3H)-dihydro pyrimidinedione-N6-oxide

Repeating Example 1 but using 1-[(6methylergolin-8β-ethyl]-2,4-(1H,3H)dihydro-pyrimidinedione instead of 1-[(6-methyl-Δ-9,10-ergolen-8β-yl)methyl]-2,4-(1H,3H)-pyrimidinedione, the title compound was obtained in 55% yield, m.p. 192–194° C.

Having now fully described the present invention, it will be apparent to one of ordinary skill in the art that many changes and modifications can be made thereto without departing from the spirit or scope of the invention as set forth herein.

What is new and desired to be secured by Letters Patent of the United States is:

1. An ergoline compound of the formula I:

wherein $R_1$ represents hydrogen or a methyl group; $R_2$ represents hydrogen or a halogen atom, a methyl, cyano or phenyl group or an alkylthio group having from 1 to about 4 carbon atoms; $R_3$ represents a hydrocarbon group having from 1 to about 4 carbon atoms; $R_4$ represents hydrogen, a phenyl group or a hydrocarbon group having from 1 to about 4 carbon atoms; wherein either (a) each of $R_6$ and $R_7$ represents a hydrogen atom or, taken together $R_6$ and $R_7$ represent a valence bond and $R_8$ represents a hydrogen atom or a methoxy group, or (b) $R_6$ represents a hydrogen atom and $R_7$ and $R_8$ taken together represent a valence bond; W represents an oxygen atom or an imino group; A represents a group of the formula $CHR_5$, $CH=CR_5$ or $CH_2CHR_5$ wherein $R_5$ represents a hydrogen atom or an alkyl group having from 1 to about 4 carbon atoms; X represents an oxygen or sulphur atom or an imino group; and n is 0, 1 or 2; or a pharmaceutically acceptable salt thereof.

2. The ergoline compound according to claim 1, wherein each of $R_1$, $R_2$, $R_4$, $R_5$ and $R_6$ represents hydrogen, n is 1, each of W and X represents an oxygen atom and $R_7$ and $R_8$ taken together represent a valence bond.

3. 1-[(6-Methyl-Δ-9,10-ergolen-8β-yl)methyl]-2,4-(1H,3H)-pyrimidinedione-N6-oxide or a pharmaceutically acceptable salt thereof.

4. 1[(6-Methyl-Δ-9,10-ergolene-8β-yl)methyl]-2,4-imidazolidinedione-N6-oxide or a pharmaceutically acceptable salt thereof.

5. An antihypertensive composition comprising an effective amount of an ergoline compound according to claim 1, or a pharmaceutically acceptable salt thereof in admixture with a pharmaceutically acceptable diluent or carrier.

6. A method of treating hypertension in a mammal, which comprises administering to said mamman an effective amount of one or more of the compounds of claim 1.

7. A method of treating hypertension in a mammal, which comprises administering to said mammal an effective amount of the composition of claim 5.

* * * * *